United States Patent

Lively et al.

[11] Patent Number: 5,584,822
[45] Date of Patent: Dec. 17, 1996

[54] EMERGENCY NOSE BLEED PACK

[76] Inventors: Bill W. Lively, 5 Woodcrest Ct., Cincinnati, Ohio 45246; Richard C. Bozian, 471 W. Galbraith Rd., Cincinnati, Ohio 45215

[21] Appl. No.: 408,342
[22] Filed: Mar. 22, 1995
[51] Int. Cl.$^6$ .................................................. A61B 17/00
[52] U.S. Cl. ............................................. 604/286; 604/285
[58] Field of Search ................................. 604/54, 285, 286, 604/358, 360, 375, 377, 385.1, 385.2

[56] References Cited

U.S. PATENT DOCUMENTS

| | | | |
|---|---|---|---|
| 732,855 | 7/1903 | Hewish | 604/286 |
| 1,608,628 | 11/1926 | Shepherd | 604/285 |
| 1,932,383 | 10/1933 | Richardson | 604/375 |
| 2,007,503 | 7/1935 | Riordan | 604/377 |
| 3,768,480 | 10/1973 | Meseck et al. | 604/375 X |
| 3,961,629 | 6/1976 | Richter et al. | 604/385.2 |
| 4,330,527 | 5/1982 | Arima et al. | |
| 4,457,756 | 7/1984 | Kern et al. | 604/286 |
| 4,820,266 | 4/1989 | Berry | |
| 4,950,280 | 8/1990 | Brennan | |
| 5,011,474 | 4/1991 | Brennan | |
| 5,079,010 | 1/1992 | Natterer | |

*Primary Examiner*—Sam Rimell
*Attorney, Agent, or Firm*—Richard C. Litman

[57] ABSTRACT

A cylindrical nasal tampon for a patient's self-application in controlling epistaxis comprises rayon, polysorbate 20, and optionally cotton fiber. A tab-like extension that is part of the tampon provides a gripping surface with which to grip the tampon. The tampon is impregnated with zinc oxide, which promotes healing, inhibits bacterial growth, limits bleeding, and prevents sticking of the tampon to the inside of the nose. The tampon is sized to be placed within the nasal cavity upon occurrence of a nosebleed. Blood from a nosebleed expands the tampon, holding it in place. When the nosebleed is ended, the tampon may be removed by applying pulling force to the extension, without disturbing blood clots that have formed.

7 Claims, 1 Drawing Sheet

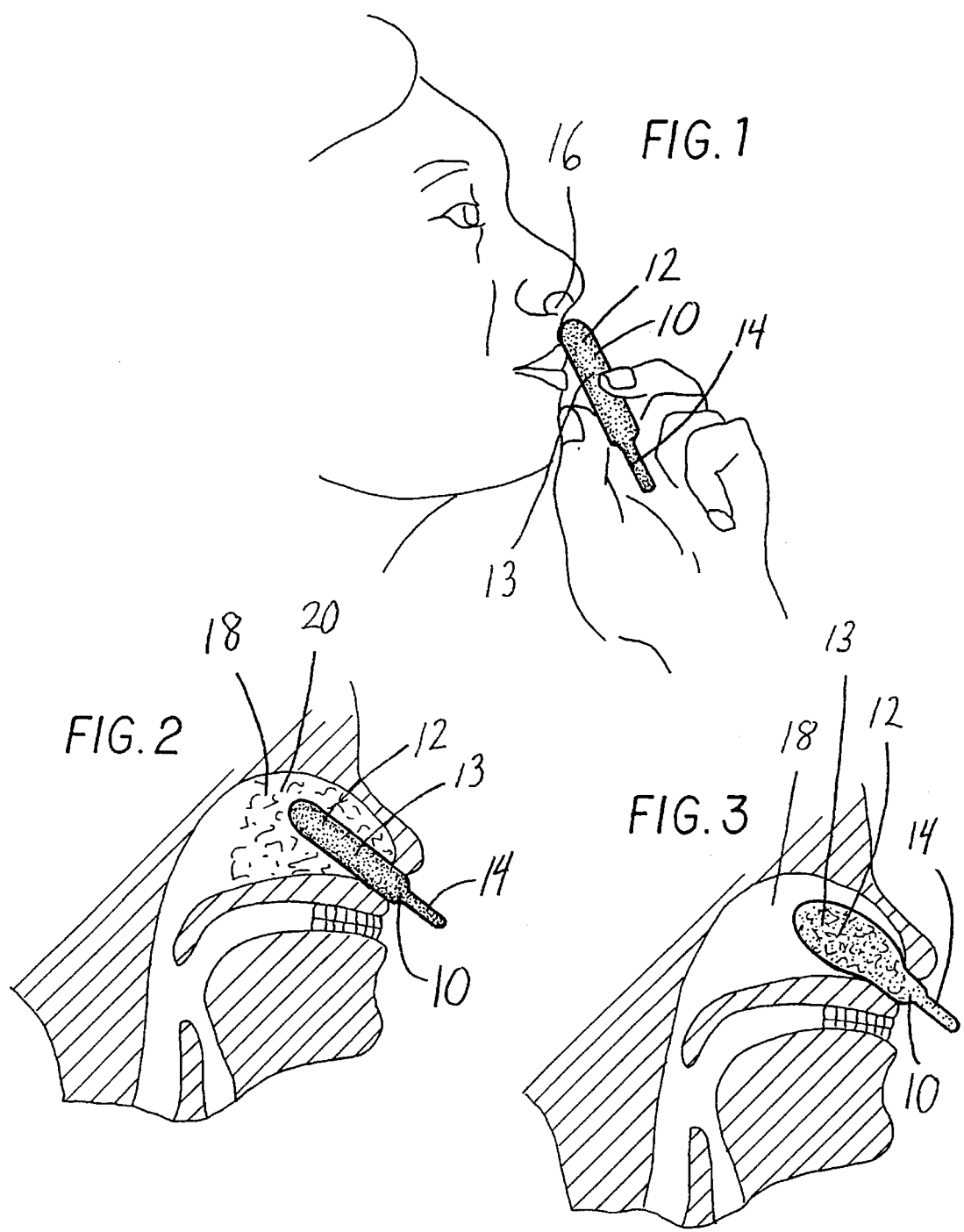

EMERGENCY NOSE BLEED PACK

BACKGROUND OF THE INVENTION

1. Field of the Invention

The present invention relates generally to epistaxis treatments, and more particularly to medicated treatments for emergent epistaxis, which can be applied without assistance.

2. Description of the Prior Art

Epistaxis, also known as "nosebleed," is a common problem. The reason that it is such a common problem is that there are so many causes of nose bleeds. Nosebleeds can be spawned by sinusitis (infection of sinus tissue), excessive drying of nasal mucous membrane, trauma (physical damage), arteriosclerosis (hardening of the arteries), hypertension (high blood pressure), and hemophilia (failure of blood to clot), among other disorders. Frequently, nosebleeds occur at unpredictable times. Moreover, nosebleeds can be dangerous events, inasmuch as loss of blood can lead to unconsciousness and death. Because of the frequency, unpredictability and danger of nose bleeds, it is critical that treatment for nose bleeds be readily available, especially for those people who have previously experienced nose bleeds. For these reasons, many attempts have been made to meet the serious need for treatment for epistaxis, but all attempts in the prior art have failed to satisfactorily meet this need. A satisfactory treatment would be effective, convenient to transport, easy to apply, and discreet. The treatment should also be pre-medicated.

U.S. Pat. No. 4,330,527, issued on May 18, 1982, to Teruo Arima, et al., describes a wound treatment agent comprised by nucleoside phosphotransferase and optionally zinc oxide. This patent does not show use of zinc oxide in cases of epistaxis, with a nasal tampon or in a nasal cavity.

U.S. Pat. No. 4,820,266, issued on Apr. 11, 1989, to Yale J. Berry, describes a method of stopping nose bleeds through use of a rigid, flattened strip. Because the strip in this patent is rough and rigid, it would be difficult to place without modification. This patent recommends soaking the strip with a liquid lubricant, which must be applied immediately before placement of the strip in the nasal cavity. As a result, use of the strip in this patent is so complicated as to be practically unusable by a traveller, for example. Using the strip in this patent also requires continuous application of pressure, which can be inconvenient and embarrassing.

U.S. Pat. No. 4,950,280, issued on Aug. 21, 1990, to H. George Brennan, describes a counter-weighted nasal tampon. The tampon of this patent is relatively complicated and thus expensive, and requires forceps and surgical assistance for insertion. There is no indication of the use of zinc oxide in this patent.

U.S. Pat. No. 5,011,474, issued on Apr. 30, 1991, to H. George Brennan, describes nasal tampon with a sealing cuff and drainage conduit. The tampon of this patent is relatively complicated and thus expensive to manufacture, and requires forceps and surgical assistance for insertion. There is no indication of the use of zinc oxide in this patent.

U.S. Pat. No. 5,079,010, issued on Jan. 7, 1992, to Siegfreid Natterer, describes a preparation for treatment of damaged tissue. The preparation of this patent comprises aqueous solution of metallic elements. There is no suggestion in this patent of the use of zinc oxide with nasal tampons.

None of the above inventions and patents, taken either singly or in combination, is seen to describe the instant invention as claimed.

SUMMARY OF THE INVENTION

A nasal tampon according to the present invention is cylindrical in shape and is suitable for a patient's self-application in controlling epistaxis. The tampon has a wedget comprised of rayon, polysorbate 20, and optionally cotton fiber. The term "wedget" is used in this application to refer to a pad dimensioned and configured to fit within the human nasal cavity. An extension from the wedget provides a place on which to grip the tampon. The tampon is impregnated with zinc oxide, which promotes healing, inhibits bacterial growth, limits bleeding, and prevents sticking of the tampon to the inside of the nose. The wedget is placed within the nasal cavity upon occurrence of a nosebleed. Blood from a nosebleed expands the wedget, thereby holding the tampon in place, at which point, external pressure need not be applied to the nose. When the nosebleed is ended, the tampon may be removed by applying force to the extension, without disturbing any blood clots that may have formed.

Accordingly, it is a principal object of the invention to provide effective treatment for epistaxis which can be applied and removed without assistance.

Another object of the invention is to provide a nasal tampon impregnated with medication that tends to counteract the deleterious consequences of epistaxis.

A further object of the invention is to provide a medicated, lubricated treatment for epistaxis that does not require user-application of medicine or lubricant to the tampon itself.

An additional object of the invention is to provide a treatment for epistaxis in which constant, continued application of pressure to the nostrils is unnecessary.

It is still another object of the invention to ensure that removal of epistaxis treatment will not promote further epistaxis.

It is yet a further object of the invention to provide epistaxis treatment that is convenient to transport and conceal.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is an environmental, perspective view of the nasal tampon according to the present invention, before insertion of the tampon into the nasal cavity.

FIG. 2 is an environmental, cross section view of the nasal tampon of the present invention, shown in a nasal cavity, immediately after insertion of the tampon into the cavity.

FIG. 3 is an environmental, cross section view of the nasal tampon of the present invention, shown in a nasal cavity, after insertion of the tampon into the cavity and subsequent to absorption of blood by the tampon.

Similar reference characters denote corresponding features consistently throughout the attached drawings.

DETAILED DESCRIPTION OF THE PREFERRED EMBODIMENTS

The common problem of epistaxis or "nosebleed," is dangerous and unpredictable. When it occurs, it requires immediate, effective treatment. Yet, immediate treatment is often unavailable because nosebleeds can develop far from an emergency room of a hospital. Additionally, a victim of a nosebleed generally does not want to go through the hassle and expense of going to an emergency room. These are among reasons that the nasal tampon of the present invention has been developed. It is small, easy-to-use, and easy-to-transport. It can be stored in a purse, or even a pocket of clothing. When needed, it can be removed from sterile packaging and applied by a victim of a nosebleed, without assistance from a medical professional, or from anyone at all. When no longer needed, the nasal tampon can simply be removed, again without assistance.

Besides having numerous advantages stemming from its physical form and arrangement, the nasal tampon of the present invention is impregnated with medicine and lubricant that promote healing, inhibit bacterial growth, limit bleeding, and prevent sticking of the tampon to the inside of the nose. Moreover, it is pre-medicated and pre-lubricated, so that a user need not fumble with medications and lubrications before applying the tampon. In this way, the tampon is not only convenient, but also highly functional and effective.

Referring to the drawings, a nasal tampon 10 according to the present invention has a cylindrical-shaped wedget 12. The term "wedget" is used in this application to refer to a pad dimensioned and configured to fit within the human nasal cavity 18. The wedget 12 comprises rayon, polysorbate twenty, and optionally cotton fiber. The rayon and cotton fiber are absorbent and preferably are specifically oriented to maintain a cylindrical shape in the wedget 12. The rayon and cotton fiber could be randomly oriented, absorbent materials or could optionally be woven. The polysorbate twenty is an emulsifier. Other polysorbates could be used, although polysorbate twenty is preferred. The wedget 12 is sized to be placed through a nostril 16 and into the nasal cavity 18 upon occurrence of a nosebleed.

There is a tab-like extension 14 depending from a first end 16 of the wedget 12. This extension 14 is comprised of the same material as the wedget 12 and can be used as a handle with which to grip the tampon 10. Because the wedget 12 and the extension 14 are comprised by the same material, manufacturing costs are reduced, as compared to a tampon having a complicated pull-string. The wedget 12 is impregnated with solid powdered zinc oxide 13, which promotes healing, inhibits bacterial growth, limits bleeding, and coats wedget 12 to prevent it from sticking to the inside of the nose. Preferably, the extension 14 is not impregnated with zinc oxide 13.

Nosebleeds are a common problem, which can be brought many causes. Regardless of the cause, a nosebleed typically results in a substantial loss of blood, which must be stanched quickly and fully, in order to avoid serious health consequences. Insertion of the nasal tampon 10 into the nasal cavity 18 brings about this stanching. Zinc oxide 13 in the wedget 12 provides lubrication, so that insertion of the tampon 10 does not worsen the epistaxis. As depicted in FIG. 3, blood 20 from a nosebleed expands the wedget 12, holding it in place and preventing additional blood loss. Additionally, zinc oxide 13 in the wedget 12 promotes healing, limits bleeding and limits bacterial growth.

When the nosebleed is ended, the wedget 12 may be removed by applying force to the extension 14, without disturbing blood clots 20 that have formed. Zinc oxide 13 in the wedget 10 ensures that blood 20 and blood clots 20 do not adhere to the tampon 10.

A preferred process for using the tampon 10 includes the steps of placing a second end of the wedget 12 into the nasal cavity 18 in which epistaxis is occurring; pinching the nostrils 16 of the nasal cavity 18 for between five minutes and ten minutes; leaving the wedget 12 in the nasal cavity 18 for between four hours and twelve hours; tapping on the wedget 12 until the wedget 12 is loosened; and pulling on the extension 14 to remove the wedget 12 from the nasal cavity 18.

It is to be understood that the present invention is not limited to the embodiments described above, but encompasses any and all embodiments within the scope of the following claims.

We claim:

1. A nasal tampon for controlling epistaxis, comprising:
   a cylindrical absorbent wedget dimensioned and configured to fit through a nostril, said wedget coated with solid zinc oxide, said wedget expanding upon the absorption of blood, and said wedget having a first end and a rounded second end,
   said first end including a flexible extension of said wedget connected to said wedget at said first end.

2. The nasal tampon according to claim 1, wherein said wedget comprises a rayon and a polysorbate.

3. The nasal tampon according to claim 2, wherein said polysorbate is polysorbate 20.

4. The nasal tampon according to claim 2, wherein said wedget further comprises cotton fiber.

5. A process of using the nasal tampon according to claim 1, comprising the steps of:
   placing said second end of said wedget into a nasal cavity in which epistaxis is occurring;
   pinching nostrils of the nasal cavity for a first predetermined period of time;
   leaving said wedget in the nasal cavity for a second predetermined period of time;
   tapping on said wedget until said wedget is loosened;
   pulling on said extension to remove said wedget from the nasal cavity.

6. The process of using the nasal tampon according to claim 5, wherein said first predetermined period of time is between five minutes and ten minutes.

7. The process of using the nasal tampon according to claim 5, wherein said second predetermined period of time is between four hours and twelve hours.

* * * * *